United States Patent [19]

Sanchez

[11] Patent Number: 5,541,151

[45] Date of Patent: Jul. 30, 1996

[54] STABILIZED DIALKYL PEROXYDICARBONATE COMPOSITIONS AND THEIR USES

[75] Inventor: Jose Sanchez, Grand Island, N.Y.

[73] Assignee: Elf Atochem North America, Inc., Philadelphia, Pa.

[21] Appl. No.: 447,514

[22] Filed: May 23, 1995

Related U.S. Application Data

[62] Division of Ser. No. 197,031, Feb. 16, 1994.

[51] Int. Cl.$^6$ .................................................. B01J 31/00
[52] U.S. Cl. ............................................................ 502/160
[58] Field of Search ............................................... 502/160

[56] References Cited

U.S. PATENT DOCUMENTS

| 3,413,277 | 11/1978 | Crano et al. | 526/230.5 |
| 3,821,273 | 6/1974 | D'Angelo | 526/230.5 |
| 5,155,192 | 10/1992 | MacLeay | 526/228 |

FOREIGN PATENT DOCUMENTS

| 56-167711 | 12/1981 | Japan . |
| 4285602 | 10/1992 | Japan . |

OTHER PUBLICATIONS

J. Am. Chem Soc., 1950, 72, 1254–1263.

*Primary Examiner*—Joseph L. Schofer
*Assistant Examiner*—Wu C. Cheng
*Attorney, Agent, or Firm*—Stanley A. Marcus; Royal E. Bright

[57] ABSTRACT

Thermally stabilized initiator compositions comprising:

(a) at least one dialkyl peroxydicarbonate, and (b) a stabilizing effective amount of a compound of Structure I:

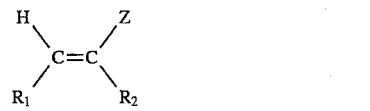

wherein $R_1$, $R_2$ and Z are as defined in the summary of the invention section, processes for their preparation and use are disclosed.

13 Claims, No Drawings

STABILIZED DIALKYL PEROXYDICARBONATE COMPOSITIONS AND THEIR USES

This is a divisional of application Ser. No. 08/197,031, filed on Feb. 16, 1994, pending.

BACKGROUND OF THE INVENTION

1. Field of the Invention

This invention relates to compositions classified in the art of chemistry as dialkyl peroxydicarbonates, more specifically to new and novel thermally-stabilized initiator compositions comprising dialkyl peroxydicarbonates stabilized by the addition thereto of a stabilizing effective amount of at least one stabilizing compound having an ethylenically unsaturated functional group conjugated with an acetylenic or nitrile functional group. The invention further relates to the use of such novel compositions as initiators of polymerization or cure of ethylenically unsaturated monomers, oligomers and polymers. The invention still further relates to the stabilization of dialkyl peroxydicarbonates during their manufacture by the inclusion of a stabilizing effective amount of at least one stabilizing compound having ethylenic unsaturation conjugated with acetylenic or nitrile unsaturation in the mixture of reactants from which a dialkyl peroxydicarbonate is to be prepared prior to, at the commencement of or during the preparative reaction.

2. Description of the Prior Art

Generally, dialkyl peroxydicarbonates which are in liquid form (molten or in solution) above ca. 10° C. are very hazardous owing to auto-accelerated decomposition attributed to induced decomposition of the dialkyl peroxydicarbonate. Strain, et al. (*J. Am. Chem. Soc.*, 1950, 72, 1254–1263) found that auto-accelerated decomposition of diisopropyl peroxydicarbonate (IPP) at room temperature could

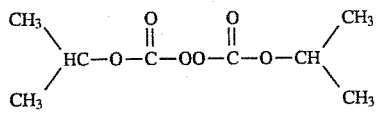

IPP be largely suppressed by incorporating small quantities of additives such as iodine (1%) phenol (1%), hydroquinone (1%), resorcinol (1%), pyrogallol (1%), tetralin (1%), ethyl acetoacetate (1%), acetanilide (1%), trinitrobenzene (1%), 30% hydrogen peroxide (1%) and several other additives. However, when such stabilizing compositions are used to polymerize vinyl chloride monomer (VCM), there is potential for contamination of the resulting PVC resin by the additives. This contamination is undesirable, both for the PVC resin as well as for the environment. Because the thermally stabilized dialkyl peroxydicarbonate compositions of the instant invention contain only small quantities of free-radically polymerizable unsaturated nitriles or unsaturated acetylenic compounds (such as methacrylonitrile), the stabilizing additives are copolymerized with VCM at very low levels (ca. 1–5 parts per million), and thus do not contaminate the PVC resin or the effluent from the polymerization process.

U.S. Pat. No. 5,155,192 discloses stabilized peroxydicarbonate compositions containing small amounts (0.03 to 3.0 equivalent percent) of compounds containing hydroperoxy groups. Such compositions are claimed to reduce sensitivity to auto-accelerative decompositions, increase safe storage temperatures and increase self-accelerating decomposition temperatures (SADTs). However, polymer producers such as PVC producers do not like to employ initiators containing significant levels of hydroperoxides such as t-butyl hydroperoxide and cumene hydroperoxide since these impurities are free-radical chain-transfer agents and can become incorporated into the resin molecular chains as peroxy end groups. Such labile end groups can adversely affect the thermal and color stability of the resin. In addition, the lower molecular weight t-alkyl hydroperoxides such as t-butyl and t-amyl hydroperoxides are sufficiently volatile to cause problems during recycle of vinyl chloride and other monomers.

The thermally stabilized dialkyl peroxydicarbonate compositions of the instant invention, which contain compounds having ethylenically unsaturated groups conjugated with nitriles or ethylenically unsaturated groups conjugated with acetylenic groups advance the peroxide art and the polymerization art since they do not cause the above resin stability problems or monomer recycle problems.

It is generally known to organic peroxide producers, see the Strain reference cited above, that lower molecular weight dialkyl peroxydicarbonates (such as diisopropyl peroxydicarbonate), which are in the liquid state during their production by reaction of an alkyl chloroformate with an aqueous solution of hydrogen peroxide and an inorganic base such as sodium hydroxide or potassium hydroxide, can be thermally stabilized and prevented from undergoing auto- or self-accelerating decomposition during manufacture by bubbling oxygen gas or an oxygen containing gas, e.g., air, through the reaction mixture. However, in such processes at least one settling of the reaction mixture into an upper organic phase (dialkyl peroxydicarbonate) and a lower aqueous phase is required. During these separations, agitation necessarily is terminated and bubbling of oxygen gas or an oxygen containing gas is stopped in order to enable complete separation of phases. During this quiescent period the organic dialkyl peroxydicarbonate phase is deprived of oxygen stabilizer and a hazardous self-accelerating decomposition of the liquid dialkyl peroxydicarbonate phase can occur.

This invention provides a novel manufacturing process of enhanced safety for production of liquid dialkyl peroxydicarbonates. The process employs a small quantity of an ethylenically unsaturated nitrile or acetylenic compound during processing for enhancing the thermal stability of the liquid dialkyl peroxydicarbonate during manufacture, thus suppressing self-accelerating decomposition of the liquid peroxydicarbonate during manufacture and enhancing the thermal stability of the liquid dialkyl peroxydicarbonate during subsequent storage and handling.

The novel processes providing enhanced safety for the manufacture, storage, handling and use of pure liquid dialkyl peroxydicarbonates can be of the batch type, continuous type or semi-continuous type.

It should be noted that the addition of the organic hydroperoxide stabilizers for dialkyl peroxydicarbonates known in the art, such as those provided by the aforementioned U.S. Pat. No. 5,155,192, during the process for production of pure liquid dialkyl peroxydicarbonates would not be effective for thermally stabilizing the dialkyl peroxydicarbonates during processing or subsequent to processing since the art organic hydroperoxide stabilizers are reactive with alkyl chloroformates, forming OO-t-alkyl O-alkyl monoperoxycarbonates:

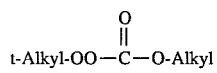

which are not known stabilizers for dialkyl peroxydicarbonates. Furthermore, many of the organic hydroperoxides of the art are likely to partition into the aqueous phases that are involved in dialkyl peroxydicarbonate manufacturing processes, and, thus, the thermal stabilizers would not be present in the organic dialkyl peroxydicarbonate phase where thermal stabilization is needed. Therefore, the stabilizing compounds having an ethylenic unsaturated functional group conjugated with an acetylenic or nitrile functional group, especially the unsaturated nitriles or the unsaturated acetylenic compounds of Structure I of this invention are also superior to the stabilizers previously known for thermally stabilizing dialkyl peroxydicarbonates during production.

DEFINITIONS

As used herein and in the appended claims the following terms have the meanings herein set forth:

Substantially pure means at least about 95% pure.

Stabilizing effective amount means from about 0.05% to about 1.4%, preferably about 0.10% to about 1.0% by weight, based on the weight of dialkyl peroxydicarbonate, of a compound of Structure I. In the case of stabilization of a liquid dialkyl peroxy dicarbonate during its preparation, stabilizing effective amount means the above stated range of amounts of a compound of Structure I added to the reaction calculated on the theoretical yield of dialkyl peroxy dicarbonate expected from the reaction. Mixtures of stabilizing conjugated unsaturated compounds, such as those of Structure I may also be employed in the same total quantity proportions.

SUMMARY OF THE INVENTION

The invention provides in a first composition aspect, a dialkyl peroxydicarbonate, containing a stabilizing effective amount of at least one compound having the Structure I:

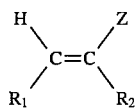

wherein $R_1$ and $R_2$ are the same or different and are selected from the group consisting of hydrogen, alkyl of 1 to 4 carbons, cycloalkyl of 5 to 10 carbons, aryl of 6 to 10 carbons, aralkyl of 7 to 11 carbons, alkenyl of 2 to 6 carbons, bromo and chloro; and wherein Z is —C≡N or —C≡C—$R_3$, wherein $R_3$ is selected from the group consisting of hydrogen, alkyl of 1 to 4 carbons, cycloalkyl of 5 to 10 carbons, alkenyl of 2 to 4 carbons, aralkyl of 7 to 11 carbons and aryl of 6 to 10 carbons.

Special mention is made of those compounds of Structure I wherein $R_1$ and $R_2$ are the same or different and are selected from the group consisting of hydrogen, alkyl of 1 to 4 carbons, aryl of 6 to 10 carbons, and alkenyl of 2 to 6 carbons, bromo and chloro. More particularly, mention is made of those compounds of Structure I wherein $R_1$ and $R_2$ are the same or different and are selected from the group consisting of hydrogen, alkyl of 1 to 4 carbons and alkenyl of 2 to 6 carbons, and of those wherein $R_1$ additionally is aryl of 6 to 9 carbons and those wherein $R_2$ additionally is chloro. Still more particularly, mention is made of compounds wherein $R_3$ is selected from the group consisting of hydrogen, alkyl of 1 to 4 carbons, alkenyl of 2 to 4 carbons, and aryl of 6 to 10 carbons. Still more particularly, mention is made of those compounds wherein $R_3$ is selected from the group consisting of hydrogen and alkyl of 1 to 4 carbons.

Particular mention is also made of compositions of the first composition aspect of the invention wherein the dialkyl peroxydicarbonate is selected from compounds having the Structure II:

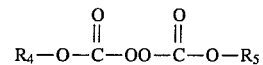 II wherein $R_4$ and $R_5$ are the same or different and are selected from the group consisting of substituted or unsubstituted alkyl of 2 to 22 carbons, substituted or unsubstituted cyclcoalkyl of 5 to 12 carbons, substituted or unsubstituted bicycloalkyl of 7 to 9 carbons, and substituted or unsubstituted aralkyl of 7 to 12 carbons, with substituents for alkyl being one or more alkyl of 1 to 4 carbons, alkoxy of 1 to 6 carbons or phenoxy, substituents for cycloalkyl being one or more alkyl of 1 to 6 carbons, substituents for bicycloalkyl being one or more alkyl of 1 to 4 carbons and substituents for aralkyl being one or more alkyl of 1 to 4 carbons, chloro, bromo, methoxy and carboxy. Further mention is made of compositions wherein either or both $R_4$ and $R_5$ are selected from the group consisting of substituted or unsubstituted alkyl radicals of 2 to 22 carbons, preferably 2 to 18 carbons, more preferably 3 to 16 carbons, substituents being alkyl radicals of 1 to 4 carbons, alkoxy radicals of 1 to 6 carbons or phenoxy radicals. Further mention is also made of compositions wherein either or both of $R_4$ and $R_5$ are selected from substituted or unsubstituted cycloalkyl radicals of 5 to 12 carbons, preferably 5 to 7 carbons, substituents being one or more alkyl radicals of 1 to 6 carbons.

Mention is also made of compositions of the first composition aspect of the invention additionally comprising from about 0.10% to about 1.0% based on weight of dialkyl peroxydicarbonate of at least one hydroperoxide known in the art as a stabilizer for dialkyl peroxydicarbonates.

The invention provides in a first process aspect, a process for polymerization of ethylenically unsaturated compounds comprising treating one or more ethylenically unsaturated compounds with an amount of at least one composition of the first composition aspect of the invention sufficient to initiate polymerization under conditions of time temperature and pressure sufficient to initiate polymerization.

Special mention is made of processes of the first process aspect of the invention wherein at least one of the unsaturated compounds to be polymerized is selected from the group consisting of an unsaturated polyester resin blend, vinyl chloride, styrene, diethylene bis(allyl carbonate), and wherein the percarbonate is selected from at least one compound having Structure II.

The invention provides in a second process aspect, a process for preparing a thermally-stabilized initiator composition of the first composition aspect of the invention which comprises reacting at least one alkyl chloroformate and aqueous hydrogen peroxide under conditions effective to form the dialkyl peroxydicarbonate in the presence of a stabilizing effective amount of at least one compound having Structure I.

As stated above, the thermally-stabilized dialkyl peroxydicarbonate initiator compositions of this invention may optionally contain from about 0.10% to about 1.0% based on weight of the dialkyl peroxydicarbonate, of an organic hydroperoxide compound. Typical examples of useful optional organic hydroperoxide compounds are given in U.S. Pat. No. 5,155,192 (column 3, lines 16 through 33).

The stabilized dialkyl peroxydicarbonate compositions of this invention, except for the presence of a stabilizing amount of the aforedescribed compound of Structure I and any optionally included hydroperoxide, can be in the form of a liquid containing substantially pure liquid dialkyl peroxydicarbonate, can be in the form of a solid as a substantially pure solid dialkyl peroxydicarbonate, can be in the form of a solution containing 10 to 90% liquid dialkyl peroxydicarbonate, can be in the form of a dispersion containing 10 to 50% solid dialkyl peroxydicarbonate, or can be in the form of an emulsion containing 10 to 70% liquid dialkyl peroxydicarbonate. Mixtures of dialkyl peroxydicarbonates prepared by simultaneous reaction of two or more chloroformates with aqueous hydrogen peroxide are specifically contemplated by the invention.

DETAILED DESCRIPTION OF THE PREFERRED EMBODIMENTS

A. LIST OF ILLUSTRATIVE EXAMPLES

1. COMPONENTS

Non-limiting examples of suitable dialkyl peroxydicarbonates that are useful for preparing the thermally stabilized dialkyl peroxydicarbonate compositions of this invention include liquid dialkyl peroxydicarbonates [melting point (mp) below 15° C.], such as diethyl peroxydicarbonate, di-n-propyl peroxydicarbonate, diisopropyl peroxydicarbonate (mp=10° C.), di-n-butyl peroxydicarbonate, diisobutyl peroxydicarbonate, di-n-hexyl peroxydicarbonate, di-(2-ethylhexyl) peroxydicarbonate and di-(2-methoxypropyl) peroxydicarbonate, and solid dialkyl peroxydicarbonates (mp above 15° C.), such as di-(n-tridecyl) peroxydicarbonate (mp=43°–45° C.), di-(n-hexadecyl) peroxydicarbonate (mp=52° C.), dibenzyl peroxydicarbonate (mp=101°–102° C.), dicyclohexyl peroxydicarbonate (mp=46° C.), di-(cis-3,3,5-trimethylcyclohexyl) peroxydicarbonate (mp=81°–82° C.), di-(4-t-butylcyclohexyl) peroxydicarbonate (mp=91°–92° C.), dibornyl peroxydicarbonate (mp= 94°–96° C.) and di-(2-phenoxyethyl) peroxydicarbonate (mp=97°–100° C.).

The stabilizing compounds are ethylenically unsaturated nitriles or ethylenically unsaturated acetylenic compounds. While the compounds of Structure I described and claimed herein are typical, the invention specifically contemplates as a full equivalent any compound having ethylenic unsaturation conjugated with acetylenic or nitrile unsaturation and which is miscible with the dialkyl peroxydicarbonate being stabilized in concentrations capable of providing an equivalent quantity of the conjugated ethylene-acetylene or ethylene-nitrile system to that provided by the compounds of Structure I when those latter compounds are used in their contemplated concentrations. Non-limiting examples of suitable unsaturated nitriles or unsaturated acetylenic compounds of Structure I that are useful for thermally stabilizing and preparing the thermally stabilized dialkyl peroxydicarbonate compositions of this invention include acrylonitrile, methacrylonitrile, cinnamonitrile, 2-chloroacrylonitrile, 2-methyl-1-buten- 3-yne and 2,5-dimethyl-1,5-hexadien-3-yne. Other compounds falling within the general category are well known in the literature and readily prepared by methods well known to those of skill in the art.

Non-limiting examples of suitable optional organic hydroperoxide compounds that are useful for optional inclusion in the thermally stabilized dialkyl peroxydicarbonate compositions of this invention include t-butyl hydroperoxide, t-amyl hydroperoxide, t-hexyl hydroperoxide, 1,1,3,3-tetramethylbutyl hydroperoxide, cumene hydroperoxide, 3-hydroxy-1,1-dimethylbutyl hydroperoxide, 1-methylcyclohexyl hydroperoxide, 2,5-dimethyl- 2,5-dihydroperoxyhexane and 3-methyl-3-hydroperoxy-1-butyne.

Non-limiting examples of suitable solvents that may optionally be used for preparing the thermally stabilized dialkyl peroxydicarbonate solutions of this invention include odorless mineral spirits (OMS), toluene, dimethyl phthalate, dibutyl phthalate and dioctyl phthalate.

2. MANUFACTURING PROCESSES

This invention also provides a novel manufacturing process of enhanced safety for production of dialkyl peroxydicarbonates and simultaneously provides an alternate means for producing novel, stabilized dialkyl peroxydicarbonate compositions containing an amount of stabilizing compound sufficient to stabilize the dialkyl peroxydicarbonate that is from about 0.05% to about 1.4%, preferably 0.10 to 1.0% by weight, based on weight of dialkyl peroxydicarbonate, of a compound of Structure I.

The process employs a small quantity (0.05% to 1.4%, preferably 0.10 to 1.0% by weight based on dialkyl peroxydicarbonate) of a compound of Structure I during processing for enhancing the thermal stability of the dialkyl peroxydicarbonate during manufacture, thus suppressing self-accelerating decomposition of the dialkyl peroxydicarbonate during manufacture and thereby also enhancing the thermal stability of the dialkyl peroxydicarbonate during subsequent storage and handling.

The novel manufacturing process for production of dialkyl peroxydicarbonates involves the following process steps:

a) Reaction Step—A substantially pure alkyl chloroformate, or a mixture of substantially pure alkyl chloroformates, (1.8 to 2.2 moles, preferably 1.9 to 2.1 moles per mole of hydrogen peroxide) is rapidly reacted with an aqueous solution of hydrogen peroxide (1.0 mole per mole of hydrogen peroxide) and sodium hydroxide or potassium hydroxide (1.9 to 2.6, preferably 2.0 to 2.2 moles per mole of hydrogen peroxide) at about −10° C. to 30° C., preferably 0° C. to 20° C., and the reaction mass is agitated for about 15–60 minutes, preferably 20–40 minutes, at 0° C. to 30° C., preferably 0° C. to 20° C.

b) Initial organic Phase/Aqueous Phase Separation—Agitation is stopped and the reaction mass is allowed to separate into an upper organic layer and a lower aqueous layer at 0° C. to 25° C., preferably 5° C. to 20° C., over a period of 5–40 minutes, preferably 10–30 minutes. The aqueous layer is drawn off and discarded.

c) Aqueous Wash and Separation—To the crude dialkyl peroxydicarbonate from step b) is added a saturated aqueous salt solution (i.e., a saturated salt solution derived from ammonium, sodium and potassium chlorides, sulfates and phosphates, preferably sodium chloride) at 0° C. to 25° C., preferably 5° C. to 20° C., and the mixture is agitated for about 1–30 minutes at 0° C. to 25° C., preferably 5° C. to 20° C. Agitation is stopped and the reaction mass is allowed to separate into an upper organic layer and a lower aqueous layer at 0° C. to 25° C., preferably 5° C. to 20° C., over a period of 5–40 minutes, preferably 10–30 minutes. The aqueous layer is drawn off and discarded. This salt wash can be repeated or a different wash treatment can be employed, if required, to purify the dialkyl peroxydicarbonate.

d) Drying Step—The wet dialkyl peroxydicarbonate from step c) is dried over about 1–10%, preferably 5%, by weight of anhydrous sodium sulfate or anhydrous magnesium sulfate at 0° C. to 25° C., preferably 0° C. to 15° C., and the spent desiccant is separate by filtration or centrifugation at 0° C. to 25° C., preferably 0° C. to 15° C., or the wet dialkyl peroxydicarbonate is blown with a relatively dry gas (e.g., dry air) at 0° C. to 25° C., preferably 0° C. to 15° C., and filtered. The pure dialkyl peroxydicarbonate at 0° C. to 15° C. is then packed out and chilled prior to storage at about −25° C. to −5° C.

The addition of a compound of Structure I in the process can be made at any of the several steps of the process. Preferably, the addition of the compound of Structure I is made shortly before the initial organic phase\aqueous phase separation step [i.e., at the end of Step a)] and agitation is continued for 1–5 minutes at 0° C. to 30° C. At this stage of the process, the stabilizings compound of Structure I (thermal stabilizer) is present in the organic phase that contains substantially pure dialkyl peroxydicarbonate. The thermal stabilizer will remain present in the substantially pure dialkyl peroxydicarbonate phase in the subsequent steps of the process, and during storage and handling. Addition of an unsaturated nitrile, such as those included in Structure I, at the beginning of the reaction stage [i.e., at the beginning of Step a)] could result in some loss of thermal stabilizing activity owing to partial conversion of the active unsaturated nitrile to an inactive unsaturated carboxamide:

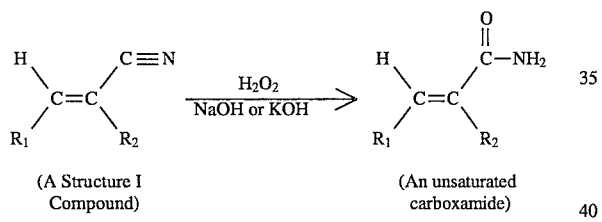

(A Structure I Compound)   (An unsaturated carboxamide)

The Room Temperature Decomposition (RTD) test methodology for determining the thermal stability of dialkyl peroxydicarbonates at about 25° C. is described in Example 1. The results in Table 1 of Example 1 show that acrylonitrile (an unsaturated nitrile of Structure I above, where $R_1$ and $R_2$ are H and Z is C≡N) is a very active thermal stabilizer for diisopropyl peroxydicarbonate whereas acrylamide (above unsaturated carboxamide, where $R_1$ and $R_2$ are H) shows no thermal stabilizing activity with diisopropyl peroxydicarbonate.

The novel processes for pure dialkyl peroxydicarbonates can be of the batch type, continuous type or semi-continuous type:

Batch Processes—For economic commercial batch processes, large reactors, agitators and cooling capacities are required, the size of each being determined by the size of the maximum reaction mass encountered during the process and the maximum heat load required during the process. Relatively large quantities of reactants and wash treatments are required. Large quantities of the product are present in crude or pure form during or at the end of the batch process. Large quantities of product are produced discontinuously at various points in time. Typical batch processes for dialkyl peroxydicarbonates are described in the chemical literature (see, for example, the Strain reference cited above).

Continuous Processes—For economic commercial continuous processes, relatively small reactors, agitators and cooling capacities are sufficient as small quantities of reactants, and wash treatments are continuously added at various stages of the process and small quantities of product are produced continuously. Once a continuous process has been established, addition of reactants and wash treatments at different points in the process and production of product are not only continuous but also simultaneous. Continuous processes are inherently safer than batch processes for production of explosively hazardous products such as organic peroxides. A continuous process for production of pure liquid dialkyl peroxydicarbonates is described in U.S. Pat. No. 3,950,375.

Semi-Continuous Processes—These processes are hybrids of batch and continuous processes, using batch processing at stages of the process where advantageous and continuous processing at stages of the process where advantageous. Generally, small reactors, agitators and cooling capacities are employed at various continuous stages of the semi-continuous processes. Larger reactors, agitators and cooling capacities are required during the batch stages of the processes. Semi-continuous processes for organic peroxides are generally less hazardous than batch processes.

It should be noted that addition of organic hydroperoxide stabilizers (as described in the previously referenced U.S. Pat. No. 5,155,192) for dialkyl peroxydicarbonates during the process for production of pure dialkyl peroxydicarbonates would not be effective for thermally stabilizing the dialkyl peroxydicarbonates during processing since such organic hydroperoxide stabilizers are reactive with alkyl chloroformates, forming OO-t-alkyl O-alkyl monoperoxycarbonates,

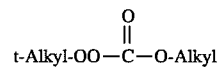

which are not known stabilizers for dialkyl peroxydicarbonates. Furthermore, many of the organic hydroperoxides are likely to partition into the aqueous phases that are involved in dialkyl peroxydicarbonate processes, and, thus would not be present in the organic dialkyl peroxydicarbonate phase where thermal stabilization is needed. Therefore, the unsaturated nitriles or the unsaturated acetylenic compounds, such as those of Structure I, of this invention are superior to the art thermal stabilizers for thermally stabilizing dialkyl peroxydicarbonates during manufacture.

3. COMPOSITIONS

Non-limiting examples of the novel, thermally stabilized dialkyl peroxydicarbonate compositions of this invention, in addition to those of the examples, include those given in Table A.

TABLE A

| Novel, Thermally-Stabilized Dialkyl Peroxydicarbonate Compositions | | |
|---|---|---|
| Thermal-Stabilizer (Structure I), Level | Peroxydicarbonate, (Structure II), Level | Other Components, Level(s) |
| Acrylonitrile, 0.50% | Diethyl, Substantially Pure | None |
| Acrylonitrile, 0.25% | Di-n-propyl, Substantially Pure | None |

TABLE A-continued

Novel, Thermally-Stabilized Dialkyl Peroxydicarbonate Compositions

| Thermal-Stabilizer (Structure I), Level | Peroxydicarbonate, (Structure II), Level | Other Components, Level(s) |
|---|---|---|
| Acrylonitrile, 0.10% | Diisobutyl, Substantially Pure | None |
| Methacrylonitrile, 1.0% | Di-n-butyl, Substantially Pure | None |
| Methacrylonitrile, 0.25% | Diisobutyl, Substantially Pure | None |
| Methacrylonitrile, 0.50% | Di-(2-ethylhexyl), Substantially Pure | None |
| Cinnamonitrile, 0.50% | Di-n-butyl, Substantially Pure | None |
| 2-Chloro-acrylonitrile 0.50% | Di-n-hexyl, Substantially Pure | None |
| 2-Methyl-1-buten-3-yne, 0.50% | Di-(2-methoxypropyl), Substantially Pure | None |
| 2,5-Dimethyl-1,5-hexadien-3-yne, 0.50% | Di-n-propyl, Substantially Pure | None |
| Methacrylonitrile, 0.30% | Di-(2-phenoxyethyl), Substantially Pure | None |
| Cinnamonitrile, 0.30% | Di-(4-t-butylcyclohexyl), Substantially Pure | None |
| Acrylonitrile, 0.50% | Di-sec-butyl, 75% | Odorless Mineral Spirits, Rest |
| Methacrylonitrile, 0.50% | Di-n-propyl, 75% | Odorless Mineral Spirits, Rest |
| 2-Methyl-1-buten-3-yne, 0.50% | Di-(2-ethylhexyl), 75% | Odorless Mineral Spirits, Rest |
| Cinnamonitrile, 0.30% | Di-sec-butyl, 60% | Dibutyl Phthalate, Rest |
| Methyacrylonitrile, 0.30% | Di-(2-ethylhexyl), 50% | Dioctyl Phthalate, Rest |

B. UTILITY

1. POLYMERIZATION OF ETHYLENICALLY UNSATURATED MONOMERS

In the free-radical polymerizations of ethylenically unsaturated monomers at suitable temperatures and pressures the novel stabilized peroxydicarbonate initiator compositions of this invention were found to be effective initiators with respect to efficiency (initiator requirements, etc.). Ethylenically unsaturated monomers include olefins, such as ethylene, propylene, styrene, alpha-methylstyrene, p-methylstyrene, chlorostyrenes, bromostyrenes, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid and methacrylic acid and their anhydrides, esters and amides, such as acrylic acid anhydride, allyl, methyl, ethyl, n-butyl, 2-hydroxyethyl, glycidyl, lauryl and 2-ethylhexyl acrylates and methacrylates, and acrylamide and methacrylamide; maleic anhydride and itaconic anhydride; maleic, itaconic and fumaric acids and their esters; vinyl halo and vinylidene dihalo compounds, such as vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, allyl ethyl carbonate, triallyl phosphate, diallyl phthalate, diallyl fumarate, diallyl glutarate, diallyl adipate, diallyl carbonate, diethylene glycol bis(allyl carbonate) (i.e., ADC); acrolein; methyl vinyl ketone; or mixtures thereof.

Temperatures of 25° C. to 100° C., preferably 30° C. to 90° C., more preferably 30° C. to 75° C. and levels of novel stabilized peroxydicarbonate initiator compositions (on a pure basis) of 0.002 to 3%, preferably 0.005% to 1%, more preferably 0.01% to 0.75% by weight based on monomer (amount effective for initiation), are normally employed in conventional polymerizations and copolymerizations of ethylenically unsaturated monomers. One of skill in the art will recognize that some of the above listed monomers will undergo polymerization at still lower temperatures in the presence of the peroxydicarbonates contemplated by this invention and that certain monomers, such as ethylene are conventionally polymerized at pressures greater than atmospheric. The processes contemplated by this invention include such conventional processing conditions. The novel stabilized peroxydicarbonate compositions of this invention can be used in combination with other free-radical initiators such as those disclosed at the bottom of column 4 and the top of column 5 of U.S. Pat. No. 4,525,308. Using the peroxide compositions of this invention in combination with these initiators adds flexibility to the processes of polymer producers and permits them to "fine tune" their polymerization processes.

2. CURING OF UNSATURATED POLYESTER RESINS

In the curing of unsaturated resin compositions (which are also ethylenically unsaturated compounds) by heating at suitable curing temperatures in the presence of free-radical curing agents, the novel stabilized peroxydicarbonate initiator compositions of this invention exhibit enhanced curing activity in the curable unsaturated polyester resin compositions. Unsaturated polyester resins that can be cured by the novel thermally stabilized dialkyl peroxydicarbonate compositions of this invention usually include an unsaturated polyester and one or more ethylenically unsaturated monomers.

The unsaturated polyesters are, for instance, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or polyols, such as ethylene glycol, diethylene glycol, triethylene glycol, 1,2- and 1,3-propanediols, 1,2-, 1,3- and 1,4-butanediols, 2,2-dimethyl-1,3-propanediol, 2-hydroxy- methyl-2-methyl-1,3-propanediol, 2-buten-1,4-diol, 2-butyn-1,4-diol, 2,4,4-trimethyl-1,3-pentanediol, glycerol, pentaerythritol, mannitol and others. Mixtures of such di- or polyacids and/or mixtures of such di- or polyols may also be used. The di- or polycarboxylic acids may be partially replaced by saturated di- or polycarboxylic acids, such as adipic acid, succinic acid, sebacic acid and other, and/or by aromatic di- or polycarboxylic acids, such as phthalic acid, trimellitic acid, pyromellitic acid, isophthalic acid and terephthalic acid. The acids used may be substituted by groups such as halogen. Examples of such suitable halogenated acids are, for instance, tetrachlorophthalic acid, tetrabromophthalic acid, 5,6-dicarboxy- 1,2, 3,4,7,7-hexachlorobicyclo(2.2.1)-2-heptene and others.

The other component of the unsaturated polyester resin composition, the polymerizable monomer or monomers, can preferably be ethylenically unsaturated monomers, such as styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl acrylate, n-butyl methacrylate, ethyl acrylate, and others, or mixtures thereof, which are copolymerizable with said unsaturated polyesters.

A preferred unsaturated polyester resin composition contains as the unsaturated polyester component the esterification product of 1,2-propanediol (a polyol), maleic anhydride (an anhydride of an unsaturated polycarboxylic acid) and phthalic anhydride (an anhydride of an aromatic dicarboxylic acid) as well as the monomer component, styrene.

Other types of unsaturated polyester resin compositions can be cured using the novel stabilized peroxydicarbonate initiator compositions of this invention as curing catalysts. These resins, called unsaturated vinyl ester resins, consist of a vinyl ester resin portion and one or more polymerizable monomer components. The vinyl ester resin component can be made by reacting a chloroepoxide, such as epichlorohydrin, with appropriate amounts of a bisphenol such as Bisphenol A [2,2-(4-hydroxyphenyl)propane], in the presence of a base, such as sodium hydroxide, to yield a condensation product having terminal epoxy groups derived from the chloroepoxide. Subsequent reaction of the condensation product with polymerizable unsaturated carboxylic acids, such as acrylic acid and methacrylic acid, in the presence or absence of acidic or basic catalysts, results in formation of the vinyl ester resin component. Normally, styrene is added as the polymerizable monomer component to complete the preparation of the unsaturated vinyl ester resin composition.

Temperatures of about 20° C. to 200° C. and levels (amounts sufficient to initiate polymerization or cure) of novel stabilized peroxydicarbonate initiator compositions of about 0.05% to 5% or more, preferably 0.10% to 4%, more preferably 0.25% to 3% by weight of curable unsaturated polyester resin composition are normally employed.

The unsaturated polyester resin compositions described above can be filled with various materials, such as sulfur, glass, carbon and boron fibers, carbon blacks, silicas, metal silicates, clays, metal carbonates, antioxidants (AO's), heat, ultraviolet (UV) and light stabilizers, sensitizers, dyes, pigments, accelerators, metal oxides, such as zinc oxide, blowing agents, nucleating agents and others.

3. CURING OF ALLYL DIGLYCOL CARBONATE (ADC) RESINS

In the curing or polymerizing of diethylene glycol bis(allyl carbonate (ADC),

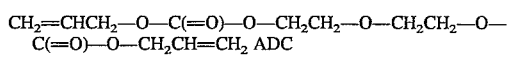

by heating ADC monomer at suitable curing temperatures in the presence of free-radical curing agents, the novel stabilized peroxydicarbonate initiator compositions of this invention exhibit enhanced curing or polymerizing activity for ADC monomer compositions. ADC was introduced commercially as CR-39™ monomer (CAS Reg. No. 142-22-3) by Pittsburgh Plate Glass Company (PPG) and is produced by reacting diethylene glycol bis(chloroformate) with allyl alcohol in the presence of alkali (R. Dowbenko, in J. I. Kroschwitz and M. Howe-Grant, eds., *Kirk-Othmer—Encyclopedia of Chemical Technology*, "Allyl Monomers and Polymers," Fourth Edition, Vol. 2, Wiley-Interscience Publication, John Wiley & Sons, Inc., New York, 1992, pp 163–168). ADC monomer can cured or polymerized alone or with other comonomers such as such as acrylic acid esters, methacrylic acid esters, allyl esters, diallyl dicarboxylates (e.g., diallyl phthalate), maleic anhydride and other monomers to produce clear castings or lenses that are transparent, tough, break-resistant and solvent-resistant. Curing or polymerizing of ADC monomer compositions are carried out in bulk (no solvent present). In general, curing or polymerizing of ADC monomer compositions to form cast sheets or lenses is carried out in two stages. The first stage involves the major part of the polymerization and occurs in the presence of the curing initiator, usually a lower dialkyl peroxydicarbonate, at temperatures of 35° C. to 120° C. Curing or polymerization times vary from about 5 hours to 50 hours. Generally a time-temperature profile is employed in the first stage. An example of a time-temperature profile is given below:

| TYPICAL CURE TEMPERATURE SCHEDULE FOR CURING OF ADC | |
|---|---|
| TIME (HOURS) | TEMPERATURE (°C.) |
| 0.0 | 61 |
| 1.0 | 62 |
| 3.0 | 64 |
| 7.0 | 68 |
| 8.0 | 69 |
| 8.5 | 74 |
| 9.0 | 79 |
| 9.5 | 86.5 |
| 10.0 | 96.5 |
| 10.5 | 115 |
| 10.75 | 85 |
| 11.0 | 60 |
| 11.25 | 40 |
| 11.5 | 30 |

The second stage of the curing or polymerizing of ADC monomer compositions involves post-curing or annealing of the ADC resin for one to several hours at 100° C. to 150° C. An example of post-curing of the ADC resin would be 2 hours at 115° C.

Levels (amounts sufficient to initiate polymerization or cure) of novel stabilized peroxydicarbonate initiator compositions of about 1% to 6% or more, preferably 2% to 5% more preferably 2.5% to 4% by weight of curable or polymerizable ADC monomer composition are normally employed.

The ADC resin compositions described above can be filled with various materials, such as antioxidants (AO's), heat, ultraviolet (UV) and light stabilizers, tints, photochromic additives and dyes. In addition, the ADC resin compositions can contain additives such as acrylic polymers and the anti-shrink, low molecular weight acrylic resins disclosed in U.S. Pat. No. 4,217,433. Such anti-shrink additives are employed to counter the 14% shrinkage that occurs when ADC monomer is polymerized.

In all cases the time, temperature and pressure conditions employed in any polymerization are not contemplated as critical by the invention and conditions normally employed by those of skill in the art may be similarly employed in the processes of this invention.

C. PREPARATIVE METHODS

PREPARATIONS OF NOVEL STABILIZED PEROXYDICARBONATE COMPOSITIONS

The dialkyl peroxydicarbonate portion of the novel, thermally stabilized peroxydicarbonate initiator compositions of this invention can be prepared by methods well known in the art (F. Strain, et al., *J. Am. Chem. Soc.*, 1950, 72, 1254–1263, and U.S. Pat. No. 3,950,375).

The compounds of Structure I are known compounds and are commercially available or may be prepared by synthetic methods well known to a skilled chemist.

The novel, stabilized peroxydicarbonate initiator compositions are prepared by thoroughly mixing 0.05% to 1.4%, preferably 0.10 to 1.0% by weight based on weight of the dialkyl peroxydicarbonate, of an unsaturated nitrile or an unsaturated acetylenic compound of Structure I with a dialkyl peroxydicarbonate at −20° C. to 20° C. Optionally, 0.10% to 1.0% by weight based on weight of the dialkyl peroxydicarbonate, of an organic hydroperoxide composition can be added to the composition.

The following examples are presented to further illustrate the best mode contemplated for the practice of the invention and to provide detailed preparative illustrations and are not intended to limit the scope of the present invention.

EXAMPLE 1

Room Temperature Decomposition Tests—Diisopropyl Peroxydicarbonate Containing Various Additives a) Sample Preparation—Samples of pure diisopropyl peroxydicarbonate and additive were prepared by stirring the additive into liquid diisopropyl peroxydicarbonate at about 15° C. until complete solution was attained (usually in less than one minute).

b) Room Temperature Decomposition (RTD) Test—10 Gram samples of the diisopropyl peroxydicarbonate compositions containing additives were placed in 5 dram vials (20 mL volume), warmed to 24° C. and were allowed to decompose. Decomposition was characterized by rapid decomposition at the liquid surface accompanied by rapid expulsion of decomposition products from the vial orifice. Once decomposition started, the contents of the vial were consumed in 10 seconds or less. The time required for onset of rapid decomposition was noted. In the case of pure diisopropyl peroxydicarbonate containing no additive, rapid decomposition occurred after 10–15 minutes. Thermally stabilizing additives significantly increased the time required for onset of rapid decomposition. An inert additive such as 1,3,5-triisopropylbenzene (1.0%) only increased the time of decomposition to 35 minutes. Table 1 tabulates the additive used, the additive level and the time to decomposition for the 10 gram samples of diisopropyl peroxydicarbonate compositions containing various additives.

TABLE 1

Thermal Stabilization of Diisopropyl Peroxydicarbonate (RTD Test)

| Additive | Additive Level, % | Decomposition Time, Mins. |
| --- | --- | --- |
| None | 0.0 | 10–15 |
| 1,3,5-Triisopropylbenzene | 1.0 | 35 |
| 2-Methyl-2-butene | 1.0 | 70 |
| 2,3-Dimethyl-2-butene | 1.0 | 275 |
|  | 0.50 | 115 |
|  | 0.25 | 45 |
| α-Methylstyrene | 1.0 | 200 |
|  | 0.50 | 95 |
|  | 0.25 | 50 |
| Isoprene | 1.0 | 320 |
|  | 0.50 | 170 |
|  | 0.25 | 70 |

TABLE 1-continued

Thermal Stabilization of Diisopropyl Peroxydicarbonate (RTD Test)

| Additive | Additive Level, % | Decomposition Time, Mins. |
| --- | --- | --- |
| Trichloroethylene | 1.0 | 140 |
| Diallyl Phthalate | 1.0 | 120 |
| Vinyl Acetate | 1.0 | 20 |
| Diethyl Maleate | 1.0 | 110 |
| t-Butyl Vinyl Ether | 1.0 | 12 |
| Acrylamide | 1.0 | 20 |
| Acrylonitrile | 1.0 | 380 |
|  | 0.50 | 290 |
|  | 0.25 | 180 |
|  | 0.10 | 100 |
| Methacrylonitrile | 1.0 | 515 |
|  | 0.50 | 300 |
|  | 0.25 | 180 |
|  | 0.10 | 95 |
| 2-Chloroacrylonitrile | 1.0 | >420 |
|  | 0.25 | 195 |
| Cinnamonitrile | 0.25 | 180 |
| Benzyl Cyanide | 0.50 | 30 |
| 2-methyl-1-buten-3-yne | 1.0 | >420 |
|  | 0.25 | 160 |
| 2,5-Dimethyl-1,5-hexadien-3-yne | 0.50 | 310 |
|  | 0.25 | 130 |
| 3-Methyl-1-butyn-3-ol | 1.0 | 35 |

The results in Table 1 show that additives with carbon-carbon double bonds (olefinic compounds; e.g., 2,3-dimethyl-2-butene), two conjugated carbon-carbon double bonds (conjugated dienes; e.g., isoprene), conjugated carbon-carbon double and carbon-carbon triple bonds (e.g., 2-methyl-1-buten-3-yne) and conjugated carbon-carbon double and carbon-nitrogen triple bonds (e.g., methacrylonitrile) increased the decomposition time for pure diisopropyl peroxydicarbonate in the RTD test. However, the most effective thermal stabilizing additives, as judged by significantly increased RTD test time at low additive levels compared to the other additives, were the thermal stabilizing additives of this invention according to Structure I, i.e., acrylonitrile, methacrylonitrile, 2-chloroacrylonitrile, cinnamonitrile, 2-methyl-1-buten-3-yne and 2,5-dimethyl-1,5-hexadien-3-yne. These were the thermal stabilizing additives with conjugated carbon-carbon double and carbon-carbon triple bonds or those with conjugated carbon-carbon double and carbon-nitrogen triple bonds.

EXAMPLE 2

Room Temperature Decomposition Tests—Di-n-propyl Peroxydicarbonate Containing Various Additives a) Sample Preparation—Samples of pure di-n-propyl peroxydicarbonate and additive were prepared by stirring the additive into liquid di-n-propyl peroxydicarbonate at about 15° C. until complete solution was attained (usually in less than one minute).

b) RTD Test—The same procedure as employed in Example 1 was employed in this example except that pure di-n-propyl peroxydicarbonate was used in place of pure diisopropyl peroxydicarbonate. 10 Gram samples of the di-n-propyl peroxydicarbonate compositions containing additives were placed in 5 dram vials (20 mL volume), warmed to 24°–26° C. and were allowed to decompose. Again, decomposition was characterized by rapid decomposition at the liquid surface accompanied by rapid expulsion of decomposition products from the vial orifice. In the case of pure di-n-propyl peroxydicarbonate containing no additive, rapid decomposition occurred after 31–38 minutes. Thermally stabilizing additives significantly increased the time required for onset of rapid decomposition. Table 2 tabulates the additive used, the additive level and the time to decomposition for the 10 gram samples of di-n-propyl peroxydicarbonate compositions containing various additives.

TABLE 2

Thermal Stabilization of Di-n-propyl Peroxydicarbonate (RTD Test)

| Additive | Additive Level, % | Decomposition Time, Mins. |
|---|---|---|
| None | 0.0 | 31–38 |
| t-Butyl Hydroperoxide (TBHP) | 0.30 | 178 |
|  | 0.20 | 80 |
|  | 0.10 | 65 |
| Methacrylonitrile (MAN) | 0.30 | 176 |
|  | 0.20 | 121 |
|  | 0.10 | 79 |
| TBHP | 0.10 |  |
| MAN | 0.20 | 174 |
| TBHP | 0.20 |  |
| MAN | 0.10 | 197 |
| Ethyl Acetoacetate | 0.30 | 89 |

The results in Table 2 show that methacrylonitrile (MAN), a thermal stabilizing additive of this invention for dialkyl peroxydicarbonates, was very effective at low use levels for thermally stabilizing di-n-propyl peroxydicarbonate as judged by significantly increased RTD test time (176 minutes) compared to the RTD test time for for pure di-n-propyl peroxydicarbonate (31–38 minutes) or the RDT test time for di-n-propyl peroxydicarbonate containing 0.30% ethyl acetoacetate (89 minutes), a previously disclosed thermal stabilizer for peroxydicarbonates (Strain reference cited above). MAN was also as effective as t-butyl hydroperoxide (TBHP), a peroxydicarbonate stabilizer of the art (U.S. Pat. No. 5,155,192). As previously mentioned, PVC producers do not like to employ initiators containing significant levels of hydroperoxides, such as t-butyl hydroperoxide and cumene hydroperoxide, as these impurities are free-radical chain-transfer agents and can become incorporated into the PVC molecular chains as peroxy end groups. Such labile end groups can adversely affect the thermal and color stability of the PVC resin. Use of MAN is not expected to cause PVC resin property problems since it should be copolymerized into the resin at very low levels (1–5 parts per million) when 0.30% MAN is employed as an additive for dialkyl peroxydicarbonates.

When MAN was used in combination with TBHP, the combinations were very effective in increasing the RTD test time for pure di-n-propyl peroxydicarbonate. Use of TBHP in combination with MAN would allow lower use levels of TBHP in PVC applications.

EXAMPLE 3

Thermal Stability Losses at 0° C./4 Weeks for Dialkyl Peroxydicarbonate Containing MAN and TBHP Samples of pure di-sec-butyl peroxydicarbonate (LUPERSOL 225, manufactured by Elf Atochem, North America, Inc.) and pure di-(2-ethylhexyl) peroxydicarbonate (LUPERSOL 223, manufactured by Elf Atochem, North America, Inc.) containing 0.30% MAN, 0.30% TBHP and combinations of MAN and TBHP were thermal stability tested in a bath held at 0° C. (32° F.) for 4 weeks. Stability tested at 0° C. for a period of 2 weeks was pure di-n-propyl peroxydicarbonate (LUPERSOL 221, manufactured by Elf Atochem, North America, Inc.), with and without 0.25% MAN. The normal recommended storage temperature for LUPERSOL 225, LUPERSOL 223 and LUPERSOL 221 are −18° C. (0° F.), −18° C. (0° F.) and −22° C. (−8° F.), respectively, therefore, the dialkyl peroxydicarbonate samples, with and without additives, were stability tested at a temperature significantly above the normal, recommended storage temperature. The results of this stability testing are summarized in Table 3.

TABLE 3

Thermal Stability Tests at 0° C./4 Weeks
Dialkyl Peroxydicarbonates with and without Additives

| Peroxydicarbonate | Additive | Additive Level, % | % Loss of Assay |
|---|---|---|---|
| Di-n-propyl | None | 0.0 | 40.5 (2 weeks) |
| Peroxydicarbonate (LUPERSOL 221) | MAN | 0.25 | 4.9 (2 weeks) |
| Di-sec-butyl | None | 0.0 | 21.3 |
| Peroxydicarbonate | MAN | 0.30 | 8.5 |
| (LUPERSOL 225) | TBHP | 0.30 | 3.9 |
|  | TBHP | 0.20 |  |
|  | MAN | 0.10 | 2.5 |
|  | TBHP | 0.10 |  |
|  | MAN | 0.20 | 0.7 |
| Di-(2-ethylhexyl) | None | 0.0 | 5.0 |
| Peroxydicarbonate | MAN | 0.30 | 0.0 |
| (LUPERSOL 223) | TBHP | 0.30 | 0.6 |
|  | TBHP | 0.20 |  |
|  | MAN | 0.10 | 0.2 |
|  | TBHP | 0.10 |  |
|  | MAN | 0.20 | 0.2 |

The results in Table 3 show that 0.25% MAN was very effective in thermally stabilizing pure LUPERSOL 221 at 0° C. In addition, 0.30% MAN, a thermal stabilizing additive of this invention for dialkyl peroxydicarbonates, very effectively reduced the assay loss for pure di-(2-ethylhexyl) peroxydicarbonate (LUPERSOL 223) at 0° C. for 4 weeks and was more effective than was 0.30% TBHP. Combinations of TBHP and MAN were also effective thermal stabilizer systems for pure LUPERSOL 223. In the case of di-sec-butyl peroxydicarbonate (LUPERSOL 225) 0.30% TBHP thermally stabilized better than did 0.30% MAN, however, the combinations of TBHP and MAN were significantly more effective in thermally stabilizing pure LUPERSOL 225 at 0° C. than was TBHP (0.30%) alone. The disadvantages of using initiators with TBHP in PVC applications was discussed in Example 2.

EXAMPLE 4

Self-Accelerating Decomposition Temperature (SADT) Test for Di-sec-butyl Peroxydicarbonate Containing 0.25% MAN The Self-Accelerating Decomposition Temperature (SADT) Test is used by organic peroxide producers to determine the lowest temperature at which an organic peroxide composition, in its largest commercial package, will undergo a self-accelerating decomposition in one week (Suggested Relative Hazard Classification of Organic Peroxides, Technical Publication, Organic Peroxide Producers Safety Division, The Society of the Plastics Industry, Inc., New York, pp. 17–20, 1992). The SADT test also evaluates the severity of the decomposition that occurs at the SADT temperature. The test is thoroughly described in the technical literature published by the Organic Peroxide Producers Safety Division (OPPSD).

SADT tests were carried out on 8 pound packages (1 gallon) of pure di-sec-butyl peroxydicarbonate (LUPERSOL 225), with and without 0.25% MAN. The SADT results obtained are summarized in Table 4.

TABLE 4

| SADT Test - Pure Di-sec-butyl Peroxydicarbonate with and without 0.25% MAN | | |
|---|---|---|
| Additive | Additive Level, % | SADT, °C. (°F.) |
| None | 0.0 | −1 (30) |
| MAN | 0.25 | 7 (45) |

The results in Table 4 show that 0.25% MAN, a thermal stabilizing additive of this invention for dialkyl peroxydicarbonates, was very effective for enhancing the thermal stability of pure di-sec-butyl peroxydicarbonate (LUPERSOL 225) as judged by significantly increased SADT temperature [from −1° C. (30° F.) to 7° C. (45° F.)].

EXAMPLE 5

Synthesis of Diisopropyl Peroxydicarbonate with 0.25% MAN Added During Synthesis Diisopropyl peroxydicarbonate (IPP) is produced commercially and is used as a free-radical initiator for polymerizing ethylenically unsaturated monomers such as vinyl chloride and for curing or polymerizing diethylene glycol bis(allyl carbonate) (ADC) monomer. The SADT for IPP (12 pound tray) is 2° C. (35° F.) whereas the melting point of IPP is about 10° C. (50° F.). Thus, IPP in the liquid state is very hazardous since its liquid temperature (at least 10° C.) is very significantly above its SADT (2° C.). Generally, it is difficult to produce a chemical composition in the solid state if its melting point is below about 25° C., therefore, such chemical compositions are processed more easily in the liquid state. Because of the difficulty in synthesizing IPP in the solid state, IPP must be produced in the liquid state at temperatures significantly above its SADT. Such processes are hazardous and there have been explosions in the production of IPP in the liquid state. The thermal stabilizer compositions of Structure I of this invention, if employed during the manufacture of dialkyl peroxydicarbonates, have potential for reducing the accelerative decomposition hazard associated with production of liquid dialkyl peroxydicarbonates such as IPP as demonstrated in Example 4 for LUPERSOL 225.

In the process for producing IPP, the following steps are generally involved:

a) Reaction Step—Isopropyl chloroformate is rapidly added to an aqueous solution of hydrogen peroxide and sodium hydroxide at about 10°–15° C. (i.e., above the melting point of pure IPP, 10° C.) and the reaction mass is stirred for about 30–60 minutes at 10°–15° C.

b) Initial Organic Phase/Aqueous Phase Separation—Stirring

Stirring is stopped and the reaction mass is allowed to separate into an upper organic layer and a lower aqueous layer at 10°–15° C. over a period of 10–15 minutes. The aqueous layer is drawn off and discarded. A self-accelerative decomposition of IPP could occur during the settling period at 10°–15° C.

c) Aqueous Wash and Separation—To the crude IPP from step b) is added an aqueous saturated sodium chloride solution at 10°–15° C. and the mixture is stirred for about 2–3 minutes at 10°–15° C. Stirring is stopped and the reaction mass is allowed to separate into an upper organic layer and a lower aqueous layer at 10°–15° C. over a period of 10–15 minutes. The aqueous layer is drawn off and discarded. A self-accelerative decomposition of IPP could also occur during this settling period at 10°–15° C.

d) Drying Step—The wet IPP from step c) is dried over about 5% by weight of anhydrous sodium sulfate or anhydrous magnesium sulfate at 10°–15° C. and the spent desiccant is separated by filtration or centrifugation at 10°–15° C. The liquid IPP at 10°–15° C. is then packed out into trays which are chilled in order to solidify IPP prior to storage at about −15° C. A self-accelerative decomposition of IPP could also occur during drying of wet IPP and pack-out of IPP at 10°–15° C.

A sample of pure IPP was prepared using the above process. At the end of the Reaction Step, 0.25% by weight of MAN, based on 70% yield of IPP, was added in order to thermally stabilize IPP during the subsequent processing. The assay of the IPP isolated was 98.8% and the corrected yield was 73.0%.

Room Temperature Decomposition (RTD) tests as described in Example 1 were carried out on IPP with no MAN, IPP with 0.25% MAN added after processing and the sample of IPP prepared in this Example (i.e., 0.25% MAN added during processing). The results are summarized in Table 5.

TABLE 5

| RTD Test - Pure Diisopropyl Peroxydicarbonate with and without 0.25% MAN | | |
|---|---|---|
| IPP Sample | MAN Level, % | Decomposition Time, Mins. |
| IPP- No MAN | 0.0 | 10–15 |
| IPP - MAN After Processing | 0.25 | 180 |
| IPP - MAN During Processing | 0.25 | 105 |

The results in Table 5 show that adding 0.25% MAN to IPP during processing has a thermal stabilizing effect on IPP as judged by significantly increased RTD time (105 minutes versus 10–15 minutes for IPP with no MAN). Hence, addition of 0.25% MAN during processing of IPP and other dialkyl peroxydicarbonates should result in reduced potential for self-accelerating decomposition of dialkyl peroxydicarbonates during and subsequent to processing.

It should be noted that the art organic hydroperoxide stabilizers for dialkyl peroxydicarbonates (U.S. Pat. No. 5,155,192) are reactive with alkyl chloroformates, forming OO-t-alkyl O-alkyl monoperoxycarbonates,

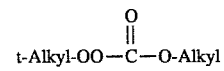

which are not known stabilizers for dialkyl peroxydicarbonates. In addition, many of the hydroperoxides partition into the aqueous phases that are involved in dialkyl peroxydicarbonate processes, and, thus are not present in the organic dialkyl peroxydicarbonate phase where thermal stabilization is needed. Therefore, the unsaturated nitriles or the unsaturated acetylenic compounds of Structure I of this invention are superior to the art thermal stabilizers for dialkyl peroxydicarbonates.

EXAMPLE 6

Vinyl Chloride Suspension Polymerization Efficiency of Diisopropyl Peroxydicarbonate Containing 0.25% MAN at 50° C. for 8 Hours.

Vinyl chloride suspension polymerizations were carried out at 50° C. over a period of 8 hours in order to determine the amounts of various IPP samples required to attain 90% conversion of vinyl chloride monomer (VCM) to poly(vinyl chloride) (PVC). The following recipe was employed in these vinyl chloride polymerizations:

| Ingredient | Parts by Weight |
|---|---|
| Vinyl Chloride Monomer | 100 |
| Water (Triple Distilled) | 130 |
| Methocel ® * (65 HG, 50 cps) (1% Aqueous Solution) | 60 |
| Aerosol MA ® ** (1% Aqueous Solution) | 60 |
| IPP Sample | Variable |

*Methylcellulose, manufactured by Dow Chemical Company.
**Sodium salt of dihexyl sulfosuccinate, manufactured by American Cyanamid Company.

Polymerization Procedure

The polymerization vessels employed in these vinyl chloride suspension polymerizations were pop bottles. Water, aqueous Methocel and aqueous Aerosol MA were added to each pop bottle and the contents were frozen at −20° C. Then to the pop bottle were added varying amounts of IPP samples (several bottles for each sample of IPP) and the required amount of liquid VCM (at −14° C.). The bottles were crown capped (with pop bottle caps), enclosed in safety cages and the caged bottles were placed in a constant temperature bottle polymerizer bath maintained at 50° C. for 8 hours. End-over-end tumbling at a rate of 25 revolutions per minute was employed for agitation. After 8 hours of agitation at 50° C., the bottles were removed, quickly cooled to 0° C. and the residual VCM was removed by venting the bottles. Venting of VCM seldom took more than 15–30 minutes; hence, post-polymerization of residual VCM was insignificant. The amount of PVC produced was determined gravimetrically (by difference in weight) and graphical plots of initiator level versus % conversion of VCM to PVC were constructed for each sample of IPP (in grams per hundred grams of VCM and in moles per hundred grams of VCM at versus % conversion). Table 6 summarizes the amount of each IPP sample that was required for 90% conversion of VCM to PVC at 50° C. for 8 hours in vinyl chloride suspension polymerizations.

TABLE 6

Vinyl Chloride Suspension Polymerization Efficiency of Diisopropyl Peroxydicarbonate, With and Without 0.25% MAN, at 50° C. for 8 Hours

| IPP Sample | IPP Required/ 100 grams of VCM at 90% Conversion | |
|---|---|---|
| | Grams | Mole (× $10^4$) |
| IPP - No MAN | 0.0267 | 1.29 |
| IPP - 0.25% MAN After Processing | 0.0285 | 1.38 |
| IPP - 0.25% MAN During Processing (from Example 5) | 0.0283 | 1.37 |

The results in Table 6 show that adding 0.25% MAN to IPP during or after processing has no significant effect on 50° C./8 hour vinyl chloride suspension polymerization efficiencies of IPP.

The subject matter which applicant regards as his invention is particularly pointed out and distinctly claimed as follows:

1. A composition comprising a dialkyl peroxydicarbonate containing from about 0.05% to about 1.4% by weight of at least one compound having the Structure I,

where $R_1$ and $R_2$ are the same or different and are selected from the group consisting of hydrogen, alkyl of 1 to 4 carbons, cycloalkyl of 5 to 10 carbons, aryl of 6 to 10 carbons, aralkyl of 7 to 11 carbons, alkenyl of 2 to 6 carbons, bromo and chloro; and Z is —C≡N or —C≡C—$R_3$, where $R_3$ is selected from the group consisting of hydrogen, alkyl of 1 to 4 carbons, cycloalkyl of 5 to 10 carbons, alkenyl of 2 to 4 carbons, aralkyl of 7 to 11 carbons and aryl of 6 to 10 carbons.

2. A composition as defined in claim 1 wherein $R_1$ and $R_2$ are the same or different and are selected from the group consisting of hydrogen, alkyl of 1 to 4 carbons, aryl of 6 to 10 carbons, alkenyl of 2 to 6 carbons, bromo and chloro; and Z is —C≡N or —C≡C—$R_3$, where $R_3$ is selected from the group consisting of hydrogen, alkyl of 1 to 4 carbons, alkenyl of 2 to 4 carbons, and aryl of 6 to 10 carbons.

3. A composition as defined in claim 2 wherein $R_1$ is selected from the group consisting of hydrogen, alkyl of 1 to 4 carbons, alkenyl of 2 to 6 carbons, and aryl of 6 to 9 carbons; $R_2$ is selected from the group consisting of hydrogen, alkyl of 1 to 4 carbons, alkenyl of 2 to 6 carbons and chloro; and Z is —C≡N or —C≡C—$R_3$, wherein $R_1$ is selected from the group consisting of hydrogen and alkyl of 1 to 4 carbons.

4. A composition as defined in claim 3 wherein the compound having Structure I is selected from the group consisting of acrylonitrile, methacrylonitrile, cinnamonitrile, 2-chloroacrylonitrile, 2-methyl-1-buten- 3-yne and 2,5-dimethyl-1,5-hexadien-3-yne.

5. A composition as defined in claim 1 wherein the dialkyl peroxydicarbonate has the Structure II:

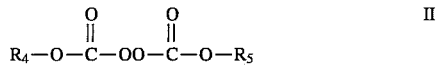

where $R_4$ and $R_5$ are the same or different and are selected from the group consisting of substituted or unsubstituted alkyl of 2 to 22 carbons, substituted or unsubstituted cycloalkyl of 5 to 12 carbons, 5 to 7 carbons, substituted or unsubstituted bicycloalkyl of 7 to 9 carbons, and substituted or unsubstituted aralkyl of 7 to 12 carbons, with substituents for alkyl being one or more alkyl of 1 to 4 carbons, alkoxy of 1 to 6 carbons, or phenoxy, substituents for cycloalkyl being one or more alkyl of 1 to 6 carbons, substituents for bicycloalkyl being one or more alkyl of 1 to 4 carbons, and substituents for aralkyl being one or more alkyl of 1 to 4 carbons, chloro, bromo, methoxy or carboxy.

6. A composition as defined in claim 5 wherein $R_4$ and $R_5$ are the same or different and are selected from the group consisting of substituted or unsubstituted alkyl and substituted or unsubstituted cycloalkyl.

7. A composition as defined in claim 6 wherein $R_4$ and $R_5$ are the same or different and are substituted or unsubstituted alkyl of 2 to 22 carbons.

8. A composition as defined in claim 1 wherein the dialkyl peroxydicarbonate is selected from the group consisting of di-n-propyl peroxydicarbonate, diisopropyl peroxydicarbonate, di-sec-butyl peroxydicarbonate and di-(2-ethylhexyl) peroxydicarbonate.

9. An improved process for the preparation of a dialkyl peroxydicarbonate composition wherein at least one alkyl chloroformate is reacted with aqueous hydrogen peroxide in a reaction mixture wherein the improvement comprises adding from about 0.05% to about 1.4% by weight of at least one compound of Structure I:

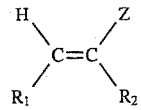

wherein $R_1$ and $R_2$ are the same or different and are selected from the group consisting of hydrogen, alkyl of 1 to 4 carbons, cycloalkyl of 5 to 10 carbons, aryl of 6 to 10 carbons, aralkyl of 7 to 11 carbons, alkenyl of 2 to 6 carbons, bromo and chloro; and, Z is $-C{\equiv}N$ or $-C{\equiv}C-R_3$, wherein $R_3$ is selected from the group consisting of hydrogen, alkyl of 1 to 4 carbons, cycloalkyl of 5 to 10 carbons, alkenyl of 2 to 4 carbons, aralkyl of 7 to 11 carbons and aryl of 6 to 10 carbons, to said reaction mixture prior to initiation of, at the time of initiation of, at any time during the reaction between said alkylchloroformate and said aqueous hydrogen peroxide, or to the dialkyl peroxydicarbonate so formed prior to or during its purification.

10. An improved process as defined in claim 9 wherein a compound of Structure I is added to the reaction mixture at the end of the reaction between the dialkyl chloroformate and the aqueous hydrogen peroxide prior to separation of crude dialkyl peroxydicarbonate from the reaction mixture.

11. An improved process as defined in claim 9 wherein, subsequent to the separation of crude dialkyl peroxydicarbonate so formed from the reaction mixture, and prior to or during purification of the dialkyl peroxydicarbonate, a compound of Structure I is added to the crude dialkyl peroxydicarbonate.

12. An improved process as defined in claim 9 wherein a compound of Structure I is added to the reaction mixture prior to or at the time of initiation the reaction between the alkyl chloroformate and the aqueous hydrogen peroxide.

13. An improved process as defined in claim 9 wherein a compound of Structure I is added to the reaction mixture during the reaction of the alkyl chloroformate and the aqueous hydrogen peroxide.

* * * * *